US006774122B2

(12) United States Patent
Evans et al.

(10) Patent No.: US 6,774,122 B2
(45) Date of Patent: Aug. 10, 2004

(54) FORMULATION

(75) Inventors: John R Evans, Macclesfield (GB); Rosalind U Grundy, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/756,291

(22) Filed: Jan. 9, 2001

(65) Prior Publication Data

US 2001/0020016 A1 Sep. 6, 2001

(30) Foreign Application Priority Data

Jan. 10, 2000 (GB) .............................................. 0000313
Apr. 12, 2000 (GB) .............................................. 0008837

(51) Int. Cl.$^7$ .............................................. A61K 31/56
(52) U.S. Cl. ...................................... 514/177; 514/178
(58) Field of Search ................................ 514/177, 178

(56) References Cited

U.S. PATENT DOCUMENTS

| 2,822,316 A | 2/1958 | Richter et al. |
|---|---|---|
| 2,983,649 A | 5/1961 | Ercoli et al. |
| 3,541,209 A | 11/1970 | Neumann et al. |
| RE28,690 E * | 1/1976 | Lehmann et al. |
| 4,048,309 A | 9/1977 | Chen et al. |
| 4,048,310 A | 9/1977 | Chen et al. |
| 4,659,516 A | 4/1987 | Bowler et al. |
| 4,888,331 A | 12/1989 | Elger et al. |
| 5,095,129 A | 3/1992 | Ottow et al. |
| 5,183,814 A | 2/1993 | Dukes |
| 5,484,801 A | 1/1996 | Al-Razzak et al. |
| 5,733,902 A | 3/1998 | Schneider |
| 5,929,030 A | 7/1999 | Hamied et al. |

FOREIGN PATENT DOCUMENTS

| EP | 0 138 504 | 4/1985 |
|---|---|---|
| EP | 0 346 014 | 12/1989 |
| FR | 6241 | 9/1968 |
| GB | 817241 | 7/1959 |
| GB | 1 126 892 | 9/1968 |
| GB | 1 207 571 | 10/1970 |
| GB | 1 569 286 | 6/1980 |
| SU | 549118 | 3/1977 |
| SU | 676284 | 7/1979 |
| WO | WO 95/12383 | 5/1995 |
| WO | WO 96/19997 | 7/1996 |
| WO | WO 97/21440 | 6/1997 |
| WO | WO 97/37653 | 10/1997 |
| WO | WO 97/40823 | 11/1997 |
| WO | WO 98/11902 | 3/1998 |
| ZA | 681014 | 2/1968 |
| ZA | 682530 | 4/1968 |

OTHER PUBLICATIONS

Remington's Pharmaceutical Sciences, 18th ed., 1990, p. 219.*

(List continued on next page.)

Primary Examiner—Sreeni Padmanabhan
Assistant Examiner—San-ming Hui
(74) Attorney, Agent, or Firm—Morgan, Lewis & Bockius LLP

(57) ABSTRACT

The invention relates to a novel sustained release pharmaceutical formulation adapted for administration by injection containing the compound 7α-[9-(4,4,5,5,5-pentafluoropentylsulphinyl)nonyl]oestra-1,3,5(10)-triene-3,17β-diol, more particularly to a formulation adapted for administration by injection containing the compound 7α-[9-(4,4,5,5,5-pentafluoropentylsulphinyl)nonyl]oestra-1,3,5 (10)-triene-3,17β-diol in solution in a ricinoleate vehicle which additionally comprises at least one alcohol and a non-aqueous ester solvent which is miscible in the ricinoleate vehicle.

9 Claims, 1 Drawing Sheet

OTHER PUBLICATIONS

Davis et al., "17–Alpha–Hydroxyprogesterone–Caproate . . . with Chemically Pure Progesterone", J. Clin. Endocrinol. And Metabolism, 1955, vol. 15, pp. 923–930.

Dukes et al., "Antiuterotrophic effects of the pure antioestrogen ICI 182, 780 . . . quantitative magnetic resonance imaging"; J. Endocrinology, 1992, vol. 138, pp. 203–209.

Dukes et al., "Antiuterotrophic effects of pure antioestrogen. ICI 182,780 . . . the uterus in ovariectromized monkeys", J. Endocrinology, 1992, vol. 135, pp. 239–247.

Howell et al., "Pharmacokinetics, pharmacological and anti–tumour effects of the specific anti–oestrogen ICI 182780 in women with advanced breast cancer", British Journal of Cancer, 1996, vol. 74, pp. 300–308.

Martindale, 32nd Ed., "Alcohol", Pharmaceutical Press, 1999, pp. 1099–1101.

Martindale, 32nd Ed., "Benzoates" and "Benzyl Alcohol"; Pharmaceutical Press, 1999, pp. 1102–1104.

Martindale, 32nd Ed., "Caster Oil"; 32nd Ed., Pharmaceutical Press, 1999, p. 1560.

Migally, "Effect of Castor Oil and Benzyl Benzoate Used as a Vehicle for Antiandrogens on the Adrenal Cortex", Archives of Andrology 2, 1979 pp. 365–369.

Pellegrino, "Use of 17 α Hydroxyprogesterone Caproate in Threatened Abortion", Current Therapeutic Research, vol. 4, No. 6, Jun., 1962, pp. 301–305.

Piver et al., "Medroxyprogesterone Acetate (Depo–Provera) vs . . . Women with Metastatic Endometrial Adenocarcinoma", Cancer, vol. 45, American Cancer Society, 1980, pp. 268–272.

Riffkin et al., "Castor Oil as a Vehicle for Parenteral Administration of Steroid Hormones", Journal of Pharmaceutical Sciences, vol. 53, No. 8, Aug. 1964, pp. 891–895.

Sawada et al., "Estrogen Receptor Antagonist ICII82,780 Exacerbates Ischemic Injury in Female Mouse", Journal of Cerebral Blood Flow and Metabolism, vol. 20. No. 1, 2000, pp. 112–118.

Vidal, Le Dictionnaire, "Benzo–Dynoestryl Retard", 1998 p. 201.

Vidal, Le Dictionnaire, "Gravibinan", 1995, pp 660–661.

Vidal, Le Dictionnaire, "Parabolan", 1997, p. 1245.

Vidal, Le Dictionnaire, "Trophobolene", 1997, pp. 1706–1707.

Wakeling et al., "A Potent Specific Pure Antiestrogen with Clinical Potential", Cancer Research, 1991, vol. 51, pp. 3867–3873.

Waterton et al., "A Case of Adenomyosis in a Pigtailed Monkey . . . Treated with the Novel Pure Antiestrogen, ICI 182,780"; Laboratory Animal Science, 1993, vol. 43, No. 3, 1993, pp. 247–251.

Howell et al., "Response to a specific antioestrogen (ICI 182780) in tamoxifen–resistant breast cancer", The Lancet, Jan. 7, 1995, pp. 29–30.

Osborne et al., "Comparison of the Effects of a Pure Steroidal Antiestrogen With Those of Tamoxifen in a Model of Human Breast Cancer", Journal of the National Cancer, May 1995, vol. 87, No. 10. pp. 746–750.

Robertson et al., "A Partially–Blind, Randomised, Multi-centre Study Comparing The Anti–Tumor Effects of Single Doses (50, 125 and 250MG) of Long–Acting (LA) 'Faslodex' (ICI 182,780 With Tamoxifin in Postmenopausal Women with Primary Breast Cancer Prior to Surgery"; Abstract 28, 22nd Annual San Antonio Breast Cancer Symposium: Dec. 8–11, 1999, San Antonio, Breast Cancer Research and Treatment 1999; 57 (1; special issue); p. 31.

Mackey et al, "Tolerability of intramuscular injections of testosterone ester in oil vehicle", Human Reproduction, vol. 10, No. 4, pp., 869–865, 1995.

* cited by examiner

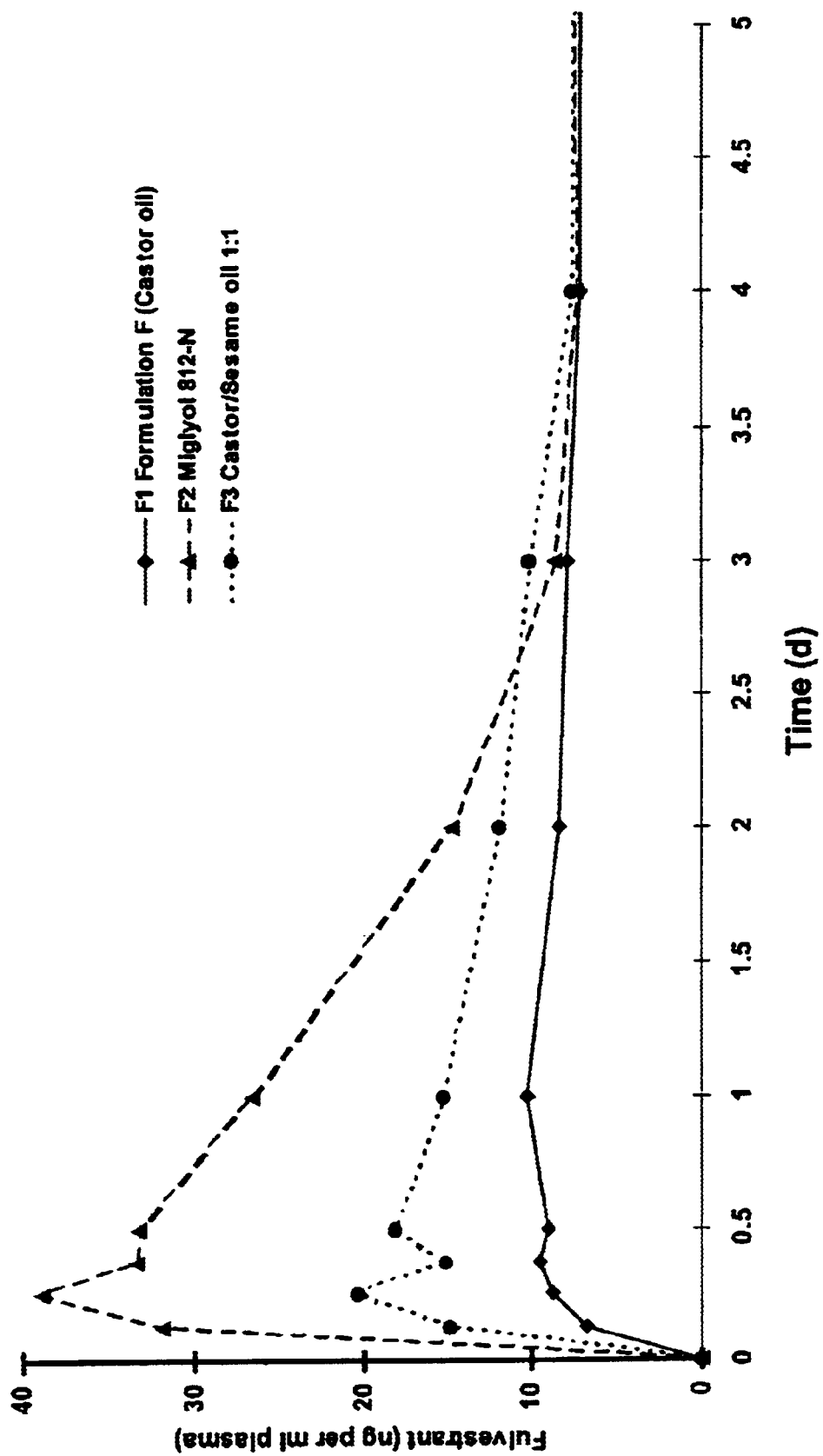

FORMULATION

The invention relates to a novel sustained release pharmaceutical formulation adapted for administration by injection containing the compound 7α-[9-(4,4,5,5,5-pentafluoropentylsulphinyl)nonyl]oestra-1,3,5(10)-triene-3,17β-diol, more particularly to a formulation adapted for administration by injection containing the compound 7α-[9-(4,4,5,5,5-pentafluoropentylsulphinyl)nonyl]oestra-1,3,5(10)-triene-3,17β-diol in solution in a ricinoleate vehicle which additionally comprises at least one alcohol and a non-aqueous ester solvent which is miscible in the ricinoleate vehicle.

Oestrogen deprivation is fundamental to the treatment of many benign and malignant diseases of the breast and reproductive tract. In premenopausal women, this is achieved by the ablation of ovarian function through surgical, radiotherapeutic, or medical means, and, in postmenopausal women, by the use of aromatase inhibitors.

An alternative approach to oestrogen withdrawal is to antagonise oestrogens with antioestrogens. These are drugs that bind to and compete for oestrogen receptors (ER) present in the nuclei of oestrogen-responsive tissue. Conventional nonsteroidal antioestrogens, such as tamoxifen, compete efficiently for ER binding but their effectiveness is often limited by the partial agonism they display, which results in an incomplete blockade of oestrogen-mediated activity (Furr and Jordan 1984, May and Westley 1987).

The potential for nonsteroidal antioestrogens to display agonistic properties prompted the search for novel compounds that would bind ER with high affinity without activating any of the normal transcriptional hormone responses and consequent manifestations of oestrogens. Such molecules would be "pure" antioestrogens, clearly distinguished from tamoxifen-like ligands and capable of eliciting complete ablation of the trophic effects of oestrogens. Such compounds are referred to as Estrogen Receptor-Downregulators (E.R.D.). The rationale for the design and testing of novel, pure antioestrogens has been described in: Bowler et al 1989, Wakeling 1990a, 1990b, 1990c. Wakeling and Bowler 1987, 1988.

Steroidal analogues of oestradiol, with an alkylsulphinyl side chain in the 7α position, provided the first examples of compounds devoid of oestrogenic activity (Bowler et al 1989). One of these, 7α-[9-(4,4,5,5,5-pentafluoropentyl sulphinyl)nonyl]oestra-1,3,5-(10)triene-3,17β-diol was selected for intensive study on the basis of its pure oestrogen antagonist activity and significantly increased antioestrogenic potency over other available antioestrogens. In vitro findings and early clinical experience with 7α-[9-(4,4,5,5,5-pentafluoropentylsulphinyl)nonyl]oestra-1,3-5(10)-triene-3,17β-diol have promoted interest in the development of the drug as a therapeutic agent for oestrogen-dependent indications such as breast cancer and certain benign gynaecological conditions.

7α-[9-(4,4,5,5,5-Pentafluoropentylsulphinyl)nonyl] oestra-1,3-5(10)-triene-3,17β-diol, or ICI 182,780, has been allocated the international non-proprietary name fulvestrant, which is used hereinafter. When referring to fulvestrant we include pharmaceutically-acceptable salts thereof and any possible solvates of either thereof.

Fulvestrant binds to ER with an affinity similar to that of oestradiol and completely blocks the growth stimulatory action of oestradiol on human breast cancer cells in vitro; it is more potent and more effective than tamoxifen in this respect. Fulvestrant blocks completely the uterotrophic action of oestradiol in rats, mice and monkeys, and also blocks the uterotrophic activity of tamoxifen.

Because fulvestrant has none of the oestrogen-like stimulatory activity that is characteristic of clinically available antioestrogens such as tamoxifen or toremifene, it may offer improved therapeutic activity characterised by more rapid, complete, or longer-lasting tumour regression; a lower incidence or rate of development of resistance to treatment; and a reduction of tumour invasiveness.

In intact adult rats, fulvestrant achieves maximum regression of the uterus at a dose which does not adversely affect bone density or lead to increased gonadotrophin secretion. If also true in humans, these findings could be of extreme importance clinically. Reduced bone density limits the duration of oestrogen-ablative treatment for endometriosis. Fulvestrant does not block hypothalamic ER. Oestrogen ablation also causes or exacerbates hot flushes and other menopausal symptoms; fulvestrant will not cause such effects because it does not cross the blood-brain barrier.

European Patent Application No. 0 138 504 discloses that certain steroid derivatives are effective antioestrogenic agents. The disclosure includes information relating to the preparation of the steroid derivatives. In particular there is the disclosure within Example 35 of the compound 7α-[9-(4,4,5,5,5-pentafluoropentylsulphinyl)nonyl]oestra-1,3,5(10)-triene-3,17β-diol, which compound is specifically named in claim 4. It is also disclosed that the compounds of that invention may be provided for use in the form of a pharmaceutical composition comprising a steroid derivative of the invention together with a pharmaceutically-acceptable diluent or carrier. It is stated therein that the composition can be in a form suitable for oral or parenteral administration.

Fulvestrant shows, along with other steroidal based compounds, certain physical properties which make formulation of these compounds difficult. Fulvestrant is a particularly lipophilic molecule, even when compared with other steroidal compounds, and its aqueous solubility is extremely low at around 10 ngml$^{-1}$ (this is an estimate from a water/solvent mixture solute since measurements this low could not be achieved in a water only solute).

Currently there are a number of sustained release injectable steroidal formulations which have been commercialised. Commonly these formulations use oil as a solvent and wherein additional excipients may be present. Below in Table 1 are described a few commercialised sustained release injectable formulations.

In the formulations within Table 1 a number of different oils are used to solubilise the compound and additional excipients such as benzyl benzoate, benzyl alcohol and ethanol have been used. Volumes of oil needed to solubilise the steroid active ingredient are low. Extended release is achievable for periods from 1 to 8 weeks.

TABLE 1

OIL BASED LONG-ACTING INTRAMUSCULAR INJECTIONS

| PRODUCT NAME | STEROID | DOSE | TYPE | COMP'. |
|---|---|---|---|---|
| SUSTANON 100 | Testosterone proprionate | 30 mg | Androgen | Organon |
| | Testosterone phenylproprionate | 60 mg | | |
| | Testosterone isocaproate | 60 mg | | |
| | Testosterone decanoate | 100 mg | | |
| PROLUTON DEPOT | Hydroxy progesterone hexanoate | 250 mgml$^{-1}$ | Progestogen | Schering HC |
| TOCOGESTAN | Hydroxy progesterone enantate | 200 mg | Progestogen | Theramax |
| | Progesterone | 50 mg | | |
| | α-Tocopherol | 250 mg | | |
| TROPHOBOLENE | Estrapronicate | 1.3 mg | Mixed | Theramax |
| | Nandrolone undecanoate | 50 mg | | |
| | Hydroxyprogesterone heptanoate | 80 mg | | |
| NORISTERAT | Norethisterone oenanthoate | 200 mg | Contraceptive | Schering HC |
| BENZO-GYNOESTRYL | Estradiol hexahydrobenzoate | 5 mg | Estradiol | Roussel |
| PROGESTERONE-RETARD | Hydroxy progesterone caproate | 250 mgml$^{-1}$ | Progestogen | Pharlon |
| GRAVIBINAN | Estradiol 17-β-valerate | 5 mgml$^{-1}$ | Mixed | Schering HC |
| | Hydroxyprogesterone caproate | 250 mgml$^{-1}$ | | |
| PARABOLAN | Trenbolone | 76 mg | Androgen | Negma |
| DELESTROGEN | Estradiol valerate | 20 mgml$^{-1}$ 40 mgml$^{-1}$ | Estradiol | BMS |
| DELALUTIN | 17-Hydroxy progesterone | 250 mgml$^{-1}$ | Progestogen | DMS |

| PRODUCT NAME | SOURCE | OIL | BzBz | BzOH | EtOH | DOSE | DOSING |
|---|---|---|---|---|---|---|---|
| SUSTANON 100 | ABPI Data Sheet Comp. 1999 | Arachis | | 0.1 ml | | 1 ml | 3 weeks |
| PROLUTON DEPOT | ABPI Data Sheet Comp. 1999 | Castor | up to 46% | | | 1 or 2 ml | 1 week |
| TOCOGESTAN | Dict. Vidal 1999 | Ethyl oleate | *40% | | | 2 ml | <1 week |
| TROPHOBOLENE | Dict. Vidal 1997 | Olive | 45% | | | 1 ml | 15 to 30 days |
| NORISTERAT | ABPI Data Sheet Comp. 1999 | Castor | YES | | | 1 ml | 8 weeks |
| BENZO-GYNOESTRYL | Dict. Vidal 1998 | Arachis | | | | 1 ml | 1 week |
| PROGESTERONE-RETARD | Dict. Vidal 1999 | Castor | YES | | | 1 or 2 ml | 1 week |
| GRAVIBINAN | Dict. Vidal 1995 | Castor | YES | | | 1 or 2 ml | 1–2 weeks |
| PARABOLAN | Dict. Vidal 1997 | Arachis | | 75 mg | 45 mg | 1.5 ml | 2 weeks |
| DELESTROGEN | J.Pharm Sci (1964) 53(8) 891 | Castor | 78% 58% | 20% 40% | 2% 2% | | |
| DELALUTIN | J.Pharm. Sci.(1964) 53(8) 891 | Castor | YES | YES | up to 2% | | |

BzBz = benzylbenzoate
BzOH = benzylalcohol
EtOH = ethanol
Dict. Vidal = Dictionnaire Vidal
% are w/v and * approximate as measured directly from a single sample described which comprises 50 mg of fulvestrant, 400 mg of benzyl alcohol and sufficient castor oil to bring the solution to a volume of 1 ml. Manufacture at a commercial scale of a formulation as described in U.S. Pat. No. 5,183,814 will be complicated by the high alcohol concentration. Therefore, there is a need to lower the alcohol concentration in fulvestrant formulations whilst preventing precipitation of fulvestrant from the formulation.

Table 2 shows the solubility of fulvestrant in a number of different solvents.

TABLE 2

SOLUBILITY OF FULVESTRANT

| SOLVENT | SOLUBILITY (mgml$^{-1}$ at 25° C.) |
|---|---|
| Water | 0.001 |
| Arachis oil | 0.45 |
| Sesame oil | 0.58 |
| Castor oil | 20 |
| Miglyol 810 | 3.06 |
| Miglyol 812 | 2.72 |
| Ethyl oleate | 1.25 |
| Benzyl benzoate | 6.15 |
| Isopropyl myristate | 0.80 |
| Span 85 (surfactant) | 3.79 |
| Ethanol | >200 |
| Benzyl Alcohol | >200 |

As can be seen fulvestrant is significantly more soluble in castor oil than any of the other oils tested. The greater solvating ability of castor oil for steroidal compounds is known and is attributed to the high number of hydroxy groups of ricinoleic acid, which is the major constituent of the fatty acids within the triglycerides present in castor oil—see (Riffkin et.al. J. Pharm. Sci., (1964), 53, 891).

However, even when using the best oil based solvent, castor oil, we have found that it is not possible to dissolve fulvestrant in an oil based solvent alone so as to achieve a high enough concentration to dose a patient in a low volume injection and achieve a therapeutically significant release rate. To achieve a therapeutically significant release rate the amount of fulvestrant needed would require the formulation volume to be large, at least 10 ml. This requires the doctor to inject an excessively large volume of formulation to administer a dose significantly high enough for human therapy.

Currently guidelines recommend that no more than 5 mls of liquid is injected intramuscularly in a single injection. Pharmacologically active doses required for a 1 month long acting depot formulation of fulvestrant is around 250 mg. Therefore, when dissolved in just castor oil, fulvestrant would need to be administered in at least 10 ml of castor oil.

The addition of organic solvents in which fulvestrant is freely soluble, and which are miscible with castor oil, may be used, such as an alcohol. With the addition of high concentrations of an alcohol concentrations of >50 mgml$^{-1}$ of fulvestrant in a castor oil formulation is achievable, thereby giving an injection volumes of <5 ml—see Table 3 below. We have surprisingly found that the introduction of a non-aqueous ester solvent which is miscible in the castor oil and an alcohol surprisingly eases the solubilisation of fulvestrant into a concentration of at least 50 mgml$^{-1}$—see Table 3 below. The finding is surprising since the solubility of fulvestrant in non-aqueous ester solvents—see Table 2 above—is significantly lower than the solubility of fulvestrant in an alcohol. The solubility of fulvestrant is also lower in non-aqueous ester solvents than is the solubility of fulvestrant in castor oil.

Therefore, we present as a feature of the invention a pharmaceutical formulation comprising fulvestrant (preferably fulvestrant is present at 3–10% w/v, 4–9% w/v, 4–8% w/v, 4–7% w/v, 4–6% w/v and most preferably at about 5% w/v) in a ricinoleate vehicle, a pharmaceutically acceptable non-aqueous ester solvent, and a pharmaceutically acceptable alcohol wherein the formulation is adapted for intra-muscular administration and attaining a therapeutically significant blood plasma fulvestrant concentration for at least 2 weeks.

Another feature of the invention is a pharmaceutical formulation comprising fulvestrant in which the formulation is adapted for intra-muscular injection into a human and which is capable after injection of attaining a therapeutically significant blood plasma fulvestrant concentration for at least 2 weeks.

Further features of the invention include a pharmaceutical formulation adapted for intra-muscular injection comprising fulvestrant, 30% or less weight of a pharmaceutically-acceptable alcohol per volume of formulation, at least 1% weight of a pharmaceutically-acceptable non-aqueous ester solvent miscible in a ricinoleate vehicle per volume of formulation and a sufficient amount of a ricinoleate vehicle so as to prepare a formulation which is capable after injection of attaining a therapeutically significant blood plasma fulvestrant concentration for at least 2 weeks.

Further features of the invention include a pharmaceutical formulation adapted for intra-muscular injection comprising fulvestrant; 35% (preferably 30% and ideally 25%) or less weight of a pharmaceutically-acceptable alcohol per volume of formulation, at least 1% (preferably at least 5% or ideally 10%) weight of a pharmaceutically-acceptable non-aqueous ester solvent miscible within a ricinoleate vehicle per volume of formulation and a sufficient amount of a ricinoleate vehicle so as to prepare a formulation of at least 45 mgml$^{-1}$ of fulvestrant.

For the avoidance of any doubt when using the term % weight per volume of formulation for the constituents of the formulation we mean that within a unit volume of the formulation a certain percentage of the constituent by weight will be present, for example a 1% weight per volume formulation will contain within a 100 ml volume of formulation 1 g of the constituent. By way of further illustration

| % of x by weight per volume of formulation | weight of x in 1 ml of formulation |
|---|---|
| 30% | 300 mg |
| 20% | 200 mg |
| 10% | 100 mg |
| 5% | 50 mg |
| 1% | 10 mg |

Preferred pharmaceutical formulations of the invention are as described above wherein:

1. The total volume of the formulation is 6 ml, or less, and the concentration of fulvestrant is at least 45 mgml$^{-1}$.
2. The total amount of fulvestrant in the formulation is 250 mg, or more, and the total volume of the formulation is 6 ml, or less.
3. The total amount of fulvestrant in the formulation is 250 mg and the total volume of the formulation is 5–5.25 ml.

It is appreciated that in the formulation an excess of formulation may be included to allow the attendant physician or care giver to be able to deliver the required dose. Therefore, when a 5 ml dose is required it would be appreciated that an excess of up to 0.25 ml, preferably up to 0.15 ml will also be present in the formulation. Typically the formulation will be presented in a vial or a prefilled syringe, preferably a prefilled syringe, containing a unit dosage of the formulation as described herein, these being further features of the invention.

Preferred concentrations of a pharmaceutically-acceptable alcohol present in any of the above formulations are; at least 3% w/v, at least 5% w/v, at least 7% w/v, at least 10% w/v, at least 11% w/v, at least 12% w/v, at least 13% w/v, at least 14% w/v, at least 15% w/v and, preferably, at least 16% w/v. Preferred maximal concentrations of pharmaceutically-acceptable alcohol present in the formulation are; 28% w/v or less, 22% w/v or less and 20% w/v or less. Preferred ranges of pharmaceutically-acceptable alcohol present in any of the above formulations are selected from any minimum or maximum value described above and preferably are; 3–35% w/v, 4–35% w/v, 5–35% w/v, 5–32% w/v, 7–32% w/v, 10–30% w/v, 12–28% w/v, 15–25% w/v, 17–23% w/v, 18–22% w/v and ideally 19–21% w/v.

The pharmaceutically-acceptable alcohol may consist of one alcohol or a mixture of two or more alcohols, preferably a mixture of two alcohols. Preferred pharmaceutically-acceptable alcohols for parenteral administration are ethanol, benzyl alcohol or a mixture of both ethanol and benzyl alcohol, preferably the ethanol and benzyl alcohol are present in the formulation in the same w/v amounts. Preferably the formulation alcohol contains 10% w/v ethanol and 10% w/v benzyl alcohol.

The pharmaceutically-acceptable non-aqueous ester solvent may consist of one or a mixture of two or more pharmaceutically-acceptable non-aqueous ester solvents, preferably just one. A preferred pharmaceutically-acceptable non-aqueous ester solvent for parenteral administration is selected from benzyl benzoate, ethyl oleate, isopropyl myristate, isopropyl palmitate or a mixture of any thereof.

The ricinoleate vehicle should preferably be present in the formulation in a proportion of at least 30% weight per volume of the formulation, ideally at least 40% or at least 50% weight per volume of formulation.

It will be understood by the skilled person that the pharmaceutically-acceptable alcohol will be of a quality such that it will meet pharmacopoeial standards (such as are described in the US, British, European and Japanese pharmacopoeias) and as such will contain some water and possibly other organic solvents, for example ethanol in the US Pharmacopeia contains not less than 94.9% by volume and not more than 96.0% by volume of ethanol when measured at 15.56° C. Dehydrated alcohol in the US Pharmacopeia contains not less than 99.5% ethanol by volume when measured at 15.56° C.

Preferred concentrations of the pharmaceutically-acceptable non-aqueous ester solvent present in any of the above formulations are; at least 5% w/v, at least 8% w/v, at least 10% w/v, at least 11% w/v, at least 12% w/v, at least 13% w/v, at least 15% w/v, at least 16% w/v, at least 17% w/v, at least 18% w/v, at least 19% w/v and at least 20% w/v. Preferred maximal concentrations of the pharmaceutically-acceptable non-aqueous ester solvent are; 60% w/v or less, 50% w/v or less, 45% w/v or less, 40% w/v or less, 35% w/v or less, 30% w/v or less and 25% w/v or less. A preferred concentration is 15% w/v. Preferred ranges of pharmaceutically-acceptable non-aqueous ester solvent present in any of the above formulations are selected from any minimum or maximum value described above and preferably are; 5–60% w/v, 7–55% w/v, 8–50% w/v, 10–50% w/v, 10–45% w/v, 10–40% w/v, 10–35% w/v, 10–30% w/v, 10–25% w/v, 12–25% w/v, 12–22% w/v, 12–20% w/v, 12–18% w/v, 13–17% w/v and ideally 14–16% w/v. Preferably the ester solvent is benzyl benzoate, most preferably at about 15% w/v.

It will be understood by the skilled person that the pharmaceutically-acceptable non-aqueous ester solvent will be of a quality that it will meet pharmacopoeial standards (such as described in the US, British, European and Japanese pharmacopoeias).

Preferred combinations of pharmaceutically-acceptable alcohol and pharmaceutically-acceptable non-aqueous ester solvent in the formulation are set out below:

| Pharmaceutically-acceptable alcohol (% w/v) | Pharmaceutically-acceptable non-aqueous ester (% w/v) |
|---|---|
| 10–30 | 5–60, 7–55, 8–50, 10–50, 10–45, 10–40, 10–35, 10–30, 10–25, 12–25, 12–22, 12–20, 12–18, 13–17 and ideally 14–16. |
| 17–23 | 5–60, 7–55, 8–50, 10–50, 10–45, 10–40, 10–35, 10–30, 10–25, 12–25, 12–22, 12–20, 12–18, 13–17 and ideally 14–16. |
| 3–35, 4–35, 5–35, 5–32, 7–32, 10–30, 12–28, 15–25, 17–23, 18–22 and ideally 19–21. | 10–35 |
| 3–35, 4–35, 5–35, 5–32, 7–32, 10–30, 12–28, 15–25, 17–23, 18–22 and ideally 19–21. | 12–18 |
| ethanol and benzyl alcohol, most preferably each at about 10% | benzyl benzoate, most preferably at about 15% |

By the use of the term ricinoleate vehicle we mean an oil which has as a proportion (at least 20%, 30%, 40%, 50%, 60%, 70%, 80%, 90% or 95% w/v) of its composition as triglycerides of ricinoleic acid. The ricinoleate vehicle may be a synthetic oil or conveniently is castor oil, ideally of pharmacopoeial standards, as described above.

We have surprisingly found that the above formulations of the invention provide, after intra-muscular injection, satisfactory release of fulvestrant over an extended period of time.

This finding is indeed surprising for the following reasons.

1. Previously tested by the applicants have been intra-muscular injections of fulvestrant in the form of an aqueous suspension. We have found extensive local tissue irritation at the injection site as well as a poor release profile. It is believed that the tissue irritation/inflammation was due to the presence of fulvestrant in the form of solid particles. The release profile appeared to be determined by the extent of inflammation/irritation present at the injection site and this was variable and difficult to control. Also the fulvestrant release rate was not sufficiently high to be clinically significant.
2. Our findings from studies using $^{14}C$ labelled benzyl alcohol show that it dissipates rapidly from the injection site and is removed from the body within 24 hours of administration.

It would be expected that ethanol will dissipate at least as quickly, if not more rapidly, from the injection site.

It is known that benzyl benzoate is metabolised by conjugation to glycine to form hippuric acid by the human liver and excreted into the urine—Martindale: The Extra Pharmacopoeia $32^{nd}$ edition page 1103, and, therefore, it is unlikely that benzyl benzoate, when used, is present at the injection site during the whole of the extended release period.

We have found that despite the rapid elimination of the additional solubilising excipients, i.e. the alcohol and pharmaceutically-acceptable non-aqueous ester solvent, from the formulation vehicle and the site of injection after injection of the formulation, extended release at therapeutically significant levels of fulvestrant over an extended period can still achieved by the formulation of the invention.

By use of the term "therapeutically significant levels" we mean that blood plasma concentrations of at least 2.5 ngml$^{-1}$, ideally at least 3 ngml$^{-1}$, at least 8.5 ngml$^{-1}$, and up to 12 ngml$^{-1}$ of fulvestrant are achieved in the patient. Preferably blood plasma levels should be less than 15 ngml$^{-1}$.

By use of the term "extended release" we mean at least two weeks, at least three weeks, and, preferably at least four weeks of continuous release of fulvestrant is achieved. In a preferred feature extended release is achieved for 36 days. Preferably extended release of fulvestrant is for at least 2–5 weeks and more preferably for the following periods (weeks) 2.5–5, 2.5–4, 3–4, 3.5–4 and most preferably for at least about 4 weeks.

It will be understood that the attendant physician may wish to administer the intra-muscular injection as a divided dose, i.e. a 5 ml formulation is sequentially administered in two separate injections of 2.5 ml, this is a further feature of the invention Simply solubilising fulvestrant in an oil based liquid formulation is not predictive of a good release profile or lack of precipitation of drug after injection at the injection site.

Table 3 shows the solubility of fulvestrant in a castor oil vehicle additionally containing alcohols ethanol and benzyl alcohol with or without benzyl benzoate. The results clearly show the positive effect of benzyl benzoate on fulvestrant solubility in castor oil, despite fulvestrant having a lower solubility in benzyl benzoate than in either alcohol or castor oil.

TABLE 3

Table 3 - EFFECT OF BENZYL BENZOATE ON FULVESTRANT SOLUBILITY IN CASTOR OIL AT 25° C.

|  | % w/v | | | | | | | |
|---|---|---|---|---|---|---|---|---|
| Ethanol (96%) | 5 | 5 | 10 | 10 | 10 | 10 | 15 | 15 |
| Benzyl Alcohol | 5 | 5 | 5 | 5 | 10 | 10 | 15 | 15 |
| Benzyl Benzoate |  | 15 |  | 15 |  | 15 |  | 15 |
| Castor Oil | to 100 | to 100 | to 100 | to 100 | to 100 | to 100 | to 100 | to 100 |
| Fulvestrant Solubility [mgml$^{-1}$] | 27 | 36 | 46 | 54 | 45 | 65 | 76 | 102 |

The following Table 4 shows the solubility of fulvestrant in a range of oil based formulations which contain the same amounts of alcohol and benzyl benzoate but in which the oil is changed. The data also shows solubility of fulvestrant after removal of the alcohols.

TABLE 4

Solubility comparisons of fulvestrant in oil based formulations with and without alcohols

| | Fulvestrant Solubility mg ml$^{-1}$ @ 25° C. | |
|---|---|---|
| Formulation[a] | Complete vehicle | Vehicle minus alcohols |
| Castor oil based | 81.2 | 12.6 |
| Miglyol 812-N based | 86.8 | 1.7 |
| Sesame seed/Castor oil (1:1) based | 70.1 | 4.4 |
| Sesame seed oil based | 45.7 | 0.7 |
| Arachis oil based | 40.2 | <0.2 |

TABLE 4-continued

Effect of formulation on precipitation of fulvestrant at the injection site

| | Days | | | | | | |
|---|---|---|---|---|---|---|---|
| Formulation[a] | 2 | 3 | 4 | 7 | 10 | 30 | 51 |
| Formulation F1 castor oil based | 0 | 0 | 0 | 0 | 0 | 0 | 0 |
| Formulation F2 Miglyol 812-N based | ++[b] | +++ | +++ | +++ | +++ | ++ | 0 |
| Formulation F3 sesame seed oil/castor oil based | +[c] | ++ | ++ | +++ | ++ | + | + |

[a]Complete Vehicle Formulations comprised ethanol [96%](10%), benzyl alcohol (10%) and benzyl benzoate (15%) made to volume with the stated oil. Excess fulvestrant was added to each solvent mixture and solubility determined.
0, +, ++, +++ = Degree of precipitation (None detected, Mild, Moderate, Severe)
[a]Formulations comprised fulvestrant (5%), ethanol [96%](10%), benzyl alcohol (10%) and benzyl benzoate (15%) made to volume with the stated oil.
[b]Mainly large needle shaped crystals
[c]Small needles and/or sheafs of crystals Precipitation of fulvestrant and the release profile was determined with the above formulations in an in vivo rabbit study.

FIG. 1 shows the release profile in vivo of the four formulations from the second part of Table 4 and shows the effect of the fixed oil component on fulvestrant plasma profile over five days following intra-muscular administration in rabbits (data normalised to 50 mg per 3 kg; mean given; number of animals per timepoint=8, plasma samples assayed for fulvestrant content using lc-ms/ms detection following solvent extraction). As can be seen the castor oil formulation showed a particularly even release profile with no evidence of precipitation of fulvestrant at the injection site.

Therefore we present as a further feature of the invention an extended release pharmaceutical formulation adapted for intra-muscular injection comprising fulvestrant; 35% (preferably 30% or ideally 25%) or less weight of a pharmaceutically-acceptable alcohol per volume of formulation, at least 1% (preferably at least 5% or ideally 10%) weight of a pharmaceutically-acceptable non-aqueous ester solvent miscible in a ricinoleate vehicle per volume of formulation and sufficient amount of a ricinoleate vehicle, taking into account the addition of any further optional pharmaceutically-acceptable excipients, so as to prepare a formulation of at least 45 mgml$^{-1}$ of fulvestrant.

A further feature of the invention is a pharmaceutical formulation adapted for intra-muscular injection, as defined above, for use in medical therapy.

A further feature of the invention is a method of treating a benign or malignant diseases of the breast or reproductive tract, preferably treating breast cancer, by administration to a human in need of such treatment by intra-muscular injection an extended release ricinoleate vehicle based pharmaceutical formulation comprising at least 45 mgml$^{-1}$ of fulvestrant; 35% (preferably 30% or ideally 25%) or less weight of a pharmaceutically-acceptable alcohol per volume of formulation, at least 1% (preferably at least 5% or ideally 10%) weight of a pharmaceutically-acceptable non-aqueous ester solvent miscible in a ricinoleate vehicle per volume of formulation.

Preferably 5 ml of the intra-muscular injection is administered.

A further feature of the invention is use of fulvestrant in the preparation of a pharmaceutical formulation as describe hereinabove, for the treatment of a benign or malignant disease of the breast or reproductive tract, preferably treating breast cancer.

Additional excipients commonly used in the formulation field including, for example, an antioxidant preservative, a colorant or a surfactant may be used. A preferred optional excipient is a surfactant.

As described above fulvestrant is useful in the treatment of oestrogen-dependent indications such as breast cancer and gynaecological conditions, such as endometriosis.

In addition to fulvestrant another similar type of molecule is currently under clinical investigation. SH-646 (11β-fluoro-7α-(14,14,15,15,15-pentafluoro-6-methyl-10-thia-6-azapentadecyl)estra-1,3,5(10)-triene-3,17β-diol) is also putatively a compound with the same mode of action as fulvestrant and has a very similar chemical structure. It is believed that the compound will also share with fulvestrant similar physical properties and therefore the current invention will also have application with this compound.

A further feature of the invention is a pharmaceutical formulation adapted for intra-muscular injection comprising 11β-fluoro-7α-(14,14,15,15,15-pentafluoro-6-methyl-10-thia-6-azapentadecyl)estra-1,3,5(10)-triene-3,17β-diol; 35% or less weight of a pharmaceutically-acceptable alcohol per volume of formulation, at least 1% weight of a pharmaceutically-acceptable non-aqueous ester solvent miscible within a ricinoleate vehicle per volume of formulation and a sufficient amount of a ricinoleate vehicle so as to prepare a formulation of at least 45 mgml$^{-1}$ of 11β-fluoro-7α-(14,14,15,15,15-pentafluoro-6-methyl-10-thia-6-azapentadecyl)estra-1,3,5(10)-triene-3,17β-diol.

Further features of the invention are those as described above but in which SH-646 is substituted for fulvestrant.

FORMULATION EXAMPLE

Fulvestrant is mixed with alcohol and benzyl alcohol, stirring until completely dissolved. Benzyl benzoate is added and the solution is made to final weight with castor oil and stirred, (for convenience weight is used rather than volume by using the weight to volume ratio). The bulk solution is overlaid with Nitrogen. The solution is sterilised by filtration using one or two filters of 0.2 μm porosity. The sterile filtrate is kept under a nitrogen overlay as it is filled under aseptic conditions into washed and depyrogenised, sterile primary containers, for example vials or pre-filled syringes. An overage is included in the primary pack to facilitate removal of the dose volume. The primary packs are overlaid with sterile nitrogen, before aseptically sealing.

See Also Process Flow Diagram Below

Quantities of each component of the formulation is chosen according to the required formulation specification, examples are described above. For example quantities are added of each component to prepare a formulation which contains 10% weight per volume of benzyl alcohol
10% weight per volume of ethanol
15% weight per volume of benzyl benzoate
250 mg of fulvestrant for each 5 ml of finished formulation
and the remaining amount as castor oil

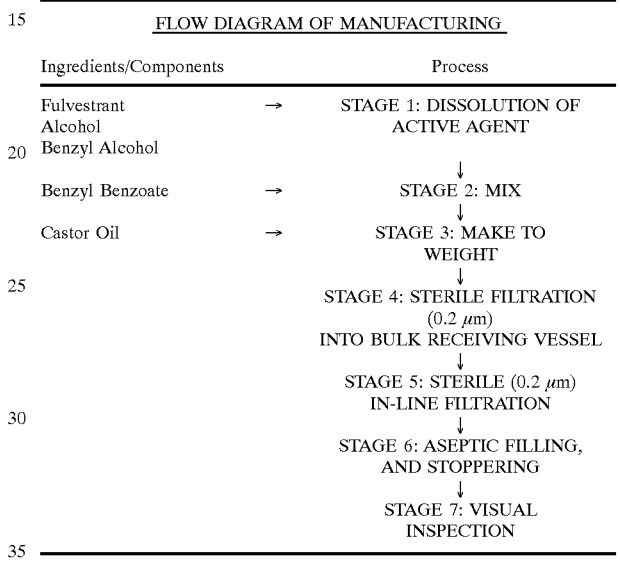

FLOW DIAGRAM OF MANUFACTURING

| Ingredients/Components | Process |
|---|---|
| Fulvestrant → | STAGE 1: DISSOLUTION OF ACTIVE AGENT |
| Alcohol | |
| Benzyl Alcohol | |
| Benzyl Benzoate → | STAGE 2: MIX |
| Castor Oil → | STAGE 3: MAKE TO WEIGHT |
| | STAGE 4: STERILE FILTRATION (0.2 μm) INTO BULK RECEIVING VESSEL |
| | STAGE 5: STERILE (0.2 μm) IN-LINE FILTRATION |
| | STAGE 6: ASEPTIC FILLING, AND STOPPERING |
| | STAGE 7: VISUAL INSPECTION |

REFERENCES

1. Bowler J, Lilley T J, Pittam J D, Wakeling A E. Novel steroidal pure antioestrogens. Steroids 989; 5471–99.
2. Wakeling A E. Novel pure antioestrogens: mode of action and therapeutic prospects. American New York Academy Science 1990a; 595: 348–56.
3. Wakeling A E. Steroidal pure antioestrogens. In Lippman M, Dickson R, editors. Regulatory mechanisms in breast cancer. Boston: Kluwer Academic, 1990b: 239–57.
4. Wakeling A E. Therapeutic potential of pure antioestrogens in the treatment of breast cancer. Journal Steroid Biochemistry 1990c; 37: 771–5.
5. Wakeling A E, Bowler J. Steroidal pure antioestrogens. Journal Endocrinology 1987; 112: R7-10.
6. Wakeling A E, Bowler J. Biology and mode of action of pure antioestrogens. Journal Steroid Biochemistry 1988; 3: 141–7.

What is claimed is:

1. A method of treating a hormonal dependent benign or malignant disease of the breast or reproductive tract by administration to a human in need of such treatment an intra-muscular injection of a pharmaceutical formulation comprising fulvestrant, a mixture of 10% weight of ethanol per volume of formulation, 10% weight of benzyl alcohol per volume of formulation and 15% weight of benzyl benzoate per volume of formulation and a sufficient amount of a castor oil vehicle, whereby a therapeutically significant blood plasma fulvestrant concentration of at least 2.5 ngml$^{-1}$ is attained for at least 2 weeks after injection.

2. The method as claimed in claim 1 wherein the benign or malignant disease is breast cancer.

3. The method as claimed in claim 1 wherein the blood plasma fulvestrant concentration is attained for at least 4 weeks after injection.

4. The method as claimed in claim 1 wherein the blood plasma fulvestrant concentration is attained for 2 to 5 weeks after injection.

5. A method of treating a hormonal dependent benign or malignant disease of the brass or reproductive tract by administration to a human in need of such treatment an intra-muscular injection of a pharmaceutical formulation comprising fulvestrant, a mixture of 10% weight of ethanol per volume of formulation, 10% weight of benzyl alcohol per volume of formulation and 15% weight of benzyl benzoate per volume of formulation and a sufficient amount of a castor oil vehicle whereby the formulation comprises at least 45 mgml of fulvestrant.

6. The method as claimed in claim 1 or 5 wherein the total volume of the formulation administered to said human is 6 ml or less, and the concentration of fulvestrant in said formulation is at least 45 $mgm^{-1}$.

7. The method as claimed in claim 1 or 5 wherein the total volume of the formulation administered to said human is 6 ml or less, and the total amount of fulvestrant in said volume of formulation is 250 mg or more.

8. The method as claimed in claim 7 wherein the total volume of formulation is from 5 to 5.25 ml, and the total amount of fulvestrant in said volume of formulation is 250 mg.

9. The method as claimed in claim 5 wherein the benign or malignant disease is breast cancer.

\* \* \* \* \*

UNITED STATES PATENT AND TRADEMARK OFFICE
CERTIFICATE OF CORRECTION

| | |
|---|---|
| PATENT NO. | : 6,774,122 B2 |
| APPLICATION NO. | : 09/756291 |
| DATED | : August 10, 2004 |
| INVENTOR(S) | : John R. Evans and Rosalind U. Grundy |

It is certified that error appears in the above-identified patent and that said Letters Patent is hereby corrected as shown below:

Column 13, line 8, "brass" should read --breast--; and line 16, "mgml" should read --mgml$^{-1}$--.

Column 14, line 4, "mgm$^{-1}$" should read --mgml$^{-1}$--.

Signed and Sealed this

Sixteenth Day of October, 2007

JON W. DUDAS
*Director of the United States Patent and Trademark Office*